(12) United States Patent
Draxton et al.

(10) Patent No.: US 7,010,461 B2
(45) Date of Patent: Mar. 7, 2006

(54) METHOD AND SYSTEM FOR REAL TIME REPORTING OF BOILER ADJUSTMENT USING EMISSION SENSOR DATA MAPPING

(75) Inventors: Dean Draxton, Park City, UT (US); Craig Gordon Stephens, Gardnerville, NE (US)

(73) Assignee: General Electric Company, Schenectady, NY (US)

( * ) Notice: Subject to any disclaimer, the term of this patent is extended or adjusted under 35 U.S.C. 154(b) by 57 days.

(21) Appl. No.: 10/773,286

(22) Filed: Feb. 9, 2004

(65) Prior Publication Data

US 2005/0177340 A1    Aug. 11, 2005

(51) Int. Cl.
*G06F 11/30*    (2006.01)
*G06F 15/00*    (2006.01)
*G21C 17/00*    (2006.01)

(52) U.S. Cl. ...................................... 702/182; 702/132
(58) Field of Classification Search ................ 702/132, 702/182
See application file for complete search history.

(56) References Cited

U.S. PATENT DOCUMENTS

| 5,722,230 A | 3/1998 | Cohen et al. |
| 5,729,968 A | 3/1998 | Cohen et al. |
| 6,397,602 B1 | 6/2002 | Vandervort et al. |
| 6,778,937 B1 * | 8/2004 | Cleary .......................... 702/132 |
| 2004/0183800 A1 * | 9/2004 | Peterson ....................... 345/440 |

* cited by examiner

*Primary Examiner*—John Barlow
*Assistant Examiner*—Sujoy Kundu
(74) *Attorney, Agent, or Firm*—Nixon & Vanderhye P.C.

(57) ABSTRACT

A method for displaying a changing combustor condition including: sensing the combustor condition in real time using a sensor array in a gas path of the combustor; generating data from the sensor array representative of the combustor condition at a plurality of positions in the gas path; transmitting the generated data to a computer system proximate to a controller for the combustor; generating a graphical representation of the real time showing combustor conditions in the gas path, and displaying the graphical representation in real time on the computer system.

20 Claims, 4 Drawing Sheets

METHOD AND SYSTEM FOR REAL TIME REPORTING OF BOILER ADJUSTMENT USING EMISSION SENSOR DATA MAPPING

BACKGROUND OF THE INVENTION

Controls for combustion boilers allow combustion engineers to optimize boiler performance. To optimize the performance of a boiler, a combustion engineer balances and lowers emissions, e.g., oxygen ($O_2$), nitrogen oxides (NOx) and carbon monoxide (CO), from the boiler. The boiler has a series of controls to adjust, for example, the amount of fuel and air supplied to a primary combustion zone in the boiler, a reburn zone, and an overfire air zone.

A boiler typically has various emissions sensors distributed in its flue gas path. The sensors generate data indicating the emission levels at the sensor locations in the boiler. For example, carbon monoxide (CO) and oxygen ($O_2$) sensors have been arranged in a grid at a downstream location of the boiler. The grid of sensors generates data indicating a profile of emissions at a plane of the flue gases where the grid is located. Sensor grid data has not been previously processed in a manner to provide real time plots of sensor grid data.

Traditionally, engineers adjust the controls for a boiler combustion system without receiving immediate feedback as to the consequences of their adjustments on emissions. Engineers do not see the results of their adjustments until after the data on emissions subsequent to the adjustments becomes available for review. It would be desirable for engineers to receive prompt emission feedback to view the influence on emissions due to adjustments being made to a boiler.

BRIEF DESCRIPTION OF THE INVENTION

The invention may be embodied as a method of presenting a changing combustor condition including: sensing the combustor condition in real time using a sensor array in a gas path of the combustor; generating data from the sensor array representative of the combustor condition at a plurality of positions in the gas path; transmitting the generated data to a computer system proximate to a controller for the combustor; generating a graphical representation of the real time showing combustor conditions in the gas path, and displaying the graphical representation in real time on the computer system.

The invention may be further embodied as a method of presenting a changing combustor condition comprising: sensing the combustor condition in real time using a sensor array in a gas path of the combustor; generating data from the sensor array representative of the combustor condition at a plurality of positions in the gas path; transmitting the generated data in real-time to a computer system proximate to a controller for the combustor; capturing the real-time data on the computer system at a location proximate to boiler controls; generating a graphical representation of the real time showing combustor conditions in the gas path, and displaying the graphical representation in real time on the computer system.

The invention may also be embodied as a system for collecting and presenting a changing combustor condition comprising: a sensor grid located in the combustion, said grid sensing the combustor condition in real time using a sensor array in a gas path of the combustor and generating data representative of the combustor condition at a plurality of positions in the gas path; a network for communicating electronic data; a computer system coupled to the network and further comprising a controller and a display, wherein said controller receives the generated data and generates a graphical representation of the real time showing combustor conditions in the gas path, and said graphical representation is presented on said display.

The invention may be also embodied as a method of adjusting a boiler having a flue gas duct comprising: sensing flue gas emissions in the gas duct with a plurality of emission sensors arranged in an array; generating a multi-dimensional graphical depiction of the flue gas emissions by plotting sensor data captured from the emission sensor; adjusting the boiler to modify the distribution of flue gases in the gas duct; generating a subsequent multidimensional graphical depiction of the flue gas emissions by plotting sensor data captured subsequent to the boiler adjustment, and repeating until the graphical depiction displays an acceptable plot of flue gas emissions.

DETAILED DESCRIPTION OF THE INVENTION

Figure 1:
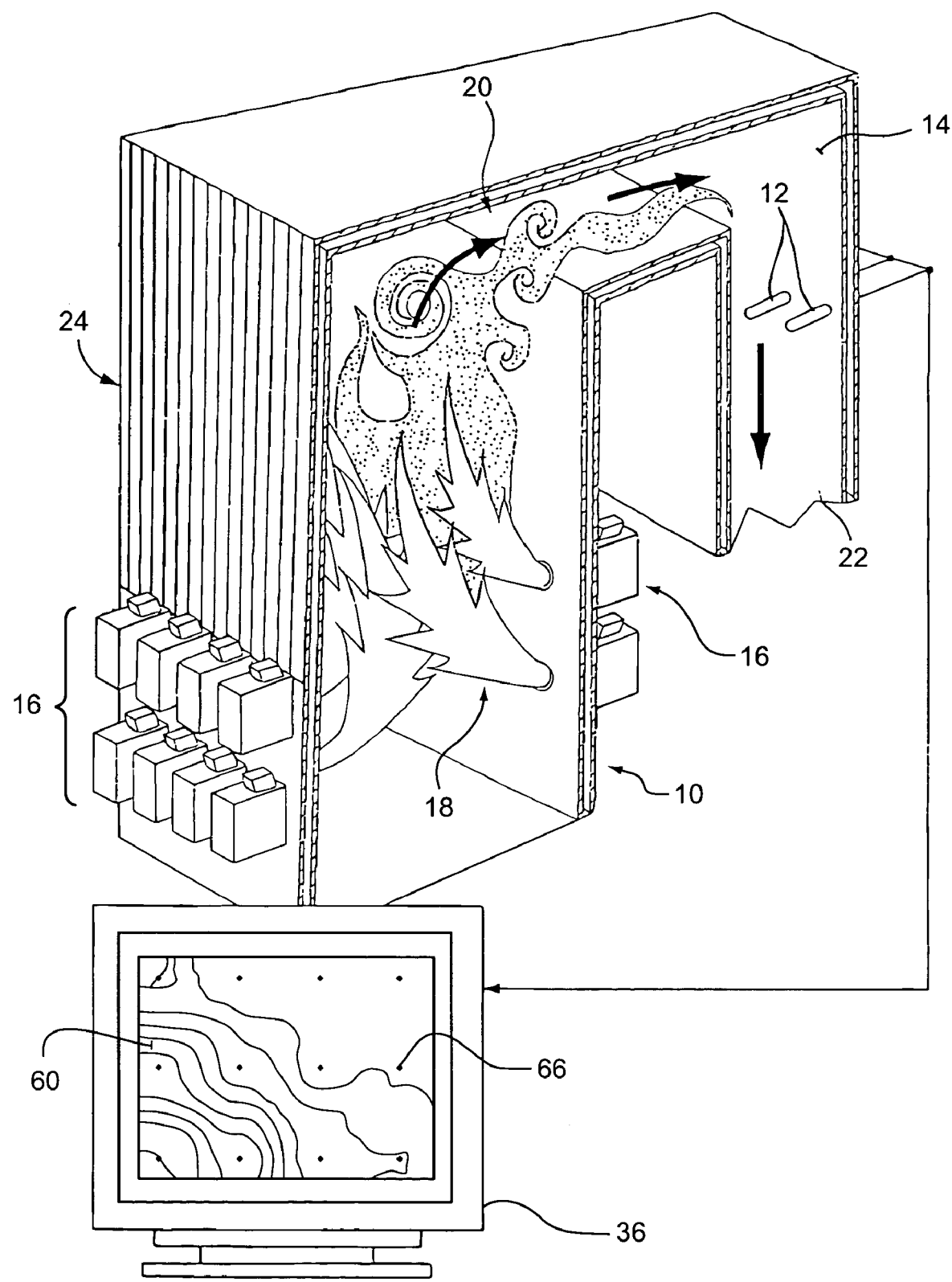
FIG. 1 is a schematic diagram of a boiler shown in cross section with a sensor grid.

FIG. 1 is a schematic cross-sectional diagram of a combustor 10, e.g., a boiler. Several in-situ carbon-monoxide (CO), oxygen ($O_2$) and temperature sensors 12 are positioned across a flue gas duct 14 of a combustor to monitor hot flue gases flowing through a post-flame zone 20. The sensors 12 may, for example, be a planer grid of solid-electrolyte sensors which measure the concentration of (or changes in the concentration of) CO, $O_2$ and temperature in the flue gases. Other sensors may also be used to measure other component gas concentrations in the flue gas or other conditions of the flue gas. The sensors generate signals indicative of the concentration of or changes in the concentration of one or more gases present in the flue gases or of the temperature of the flue gas. In practice, any number of sensors 12 may be installed across a plane in the flue gas duct 14. The sensors may be arranged in a horizontal or vertical row, in a two-dimensional (2D) or 3D grid, or in some other effective sensor pattern. The sensor may extend at varying depths into the duct to monitor a distribution profile of gaseous combustibles in the flue gas.

The combustor 10 may be a large structure, such as more than one, two or even three hundred feet tall. The combustor 10 may include a plurality of combustion devices, e.g., an assembly of combustion fuel nozzles and air injectors 16, which mix fuel and air to generate flame in a flame envelope 18 within the combustor 10. The combustion device 16 may include burners, e.g., gas-fired burners, coal-fired burners and oil-fired burners, etc. The burners may be situated in a wall-fired, opposite-fired, tangential-fired, or cyclone arrangement, and may be arranged to generate a plurality of distinct flames, a common fireball, or any combination thereof. Alternatively, a combustion device called a "stoker"

which contains a traveling or vibrating grate may be employed to generate flame within the combustor 10.

When the combustion device(s) 16 in the combustor 10 are actively burning fuel, two distinct locations can be identified within the combustor 10: (1) a flame envelope 18, and (2) a "post-flame" zone 20, which is the zone downstream of the flame envelope 18 spanning some distance toward the flue gas exit 22. Downstream of the flame envelope 18, hot combustion gases and combustion products may be turbulently thrust about. These hot combustion gases and products, collectively called "flue gas," flow from the flame envelope 18, through the "post-flame" zone and towards the exit 22 of the combustor 10. Water or other fluids (not shown) may flow through the walls 24 of the combustor 10 where they may be heated, converted to steam, and used to generate energy, for example, to drive a turbine.

The sensors 12 are located in the post-flame zone 20 of the combustor 10. The sensors 12 alternatively may be disposed in the flame envelope 18 if constructed to withstand the harsh, high-temperature environment thereof. The sensors are, in this example, a 2D grid of CO, $O_2$ and/or temperature sensors arranged at the post-flame zone 20 and in a particular plane of the flue gas path. The sensors generate data indicative of the CO, $O_2$ and/or temperature concentration at various points in a plane of the flue gas at the sensor location. Based on the data generated from each sensor, a profile can be generated of the CO emissions in the plane of the flue gas at the sensor grid location.

Figure 2:
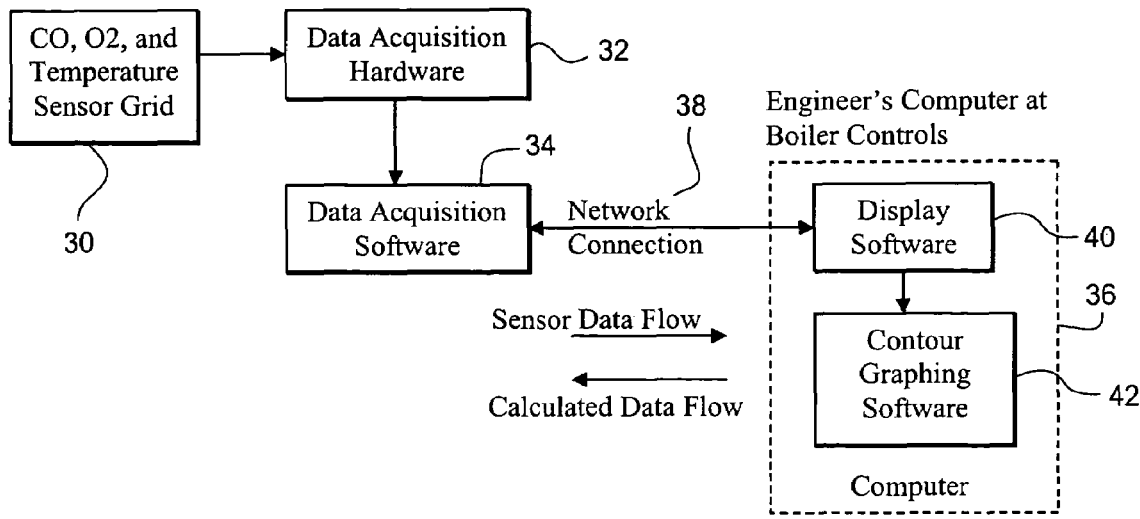
FIG. 2 is a block diagram of electronic and computer components associated with the sensor grid.

FIG. 2 is a block diagram of computer and electronic components for sensing combustion emissions; generating and processing sensor data, and plotting and otherwise presenting the sensor data. The sensor grid 30 (see exemplary sensor grid 12 in FIG. 1) is positioned at a location in the combustor to sense a condition of the combustion process and associated emissions. For example, the sensor grid may include sensors for CO, $O_2$, and/or temperature measurements of the flue gases. Each sensor in the grid 30 generates data indicative of a characteristic of the combustion process, such as the level of CO or $O_2$ emissions in the flue gas or of the temperature at a particular location in a plane of the flue gas.

The data from the sensor grid is electronically captured by data acquisition hardware 32 and associated data acquisition software 34. The sensor data is outputted by the hardware/software 32, 34 in a continuous data stream. The data may be output every ten seconds, every second, or every $1/10^{th}$ of a second (for example), to provide a real-time data output of the sensor grid.

Alternatively, the data acquisition hardware 32 may include an electronic memory to store the data generated by the sensor grid and the time at which each sensor measurement is taken. The data acquisitions hardware operates under the supervision of data acquisition software 34 to capture the sensor grid data, time stamp the data and store the data, such as in a database, for subsequent processing by a computer system 36. The sensor data stored in the data acquisition hardware 32, and accessible using the data acquisition software 34 may be formatted such that each of the sensor output values for the grid at a particular period of time is stored in a database. The data may include both (real time) data regarding the sensor output values, and historical data of prior sensor readings with associated time of reading information). Accordingly, the sensor data stored in the memory of the data acquisition hardware/software provides both real time information on sensor readings taken of the flue gases and historical sensor readings of flue gas measurements.

The computer 36 may receive a real-time output of sensor data or (alternatively) access the sensor data in the data acquisition hardware 32 by interrogating the data using the data acquisition software. The data acquisition hardware and software are well known and conventional software products. The data acquisition hardware may be a conventional computer system with electronic memory. The data acquisition software may be conventional database measurement software and software for interfacing with the sensor outputs and capturing the data in usable data form. For example, the sensor interface software may convert sensor readings into data indicative of CO and/or $O_2$ levels, and temperature levels within the flue gas stream.

The computer 36 may be, for example, a personal computer laptop computer which is carried by the boiler engineer to the control panel for the boiler, and to the side of a boiler having burner adjustment controls. The computer 36 may have a wired or wireless network connection 38 that links the computer to the data acquisition hardware/software storing the sensor data. For example, the laptop may be connected via a wired CAT5 Ethernet network (which may include a link through the Internet) to the data acquisition hardware/software unit.

The computer 36 may transmit a database interrogation request to the data acquisition software 34 to download certain sensor data stored in the data acquisition hardware. The requested sensor data may include real time sensor level outputs and historical sensor output levels. The requested data is transferred from the data acquisition hardware/software, over the network connection 38 and to the computer 36. The computer 36 may temporarily store the sensor data. The computer 36 may include conventional software modules including a display software module 40 and a mapping or graphing software module 42. The display software and graphing software in combination plots the sensor data in a contour graph or other graphical map to show the sensor data as points on the graph and arrange in a pattern substantially the same as the sensor pattern of the sensors in the grid 30.

In general, data collected from the sensor grid flows into the computer 36 which is available to the boiler engineer when adjusting the combustion conditions within the combustor. The computer 36 processes the sensor data to display to the engineer the sensor data in easily readable form, such as in a contour map showing emission levels at the sensor grid location. In addition, the computer 36 may perform other processes on the sensor data, such as calculating average emission levels based on all of the sensor output levels from the grid 30. The sensor data processed by the computer 30 is presented in a graphical display or output as calculated data which is available to the combustion engineer while adjusting the combustor.

Figure 3:
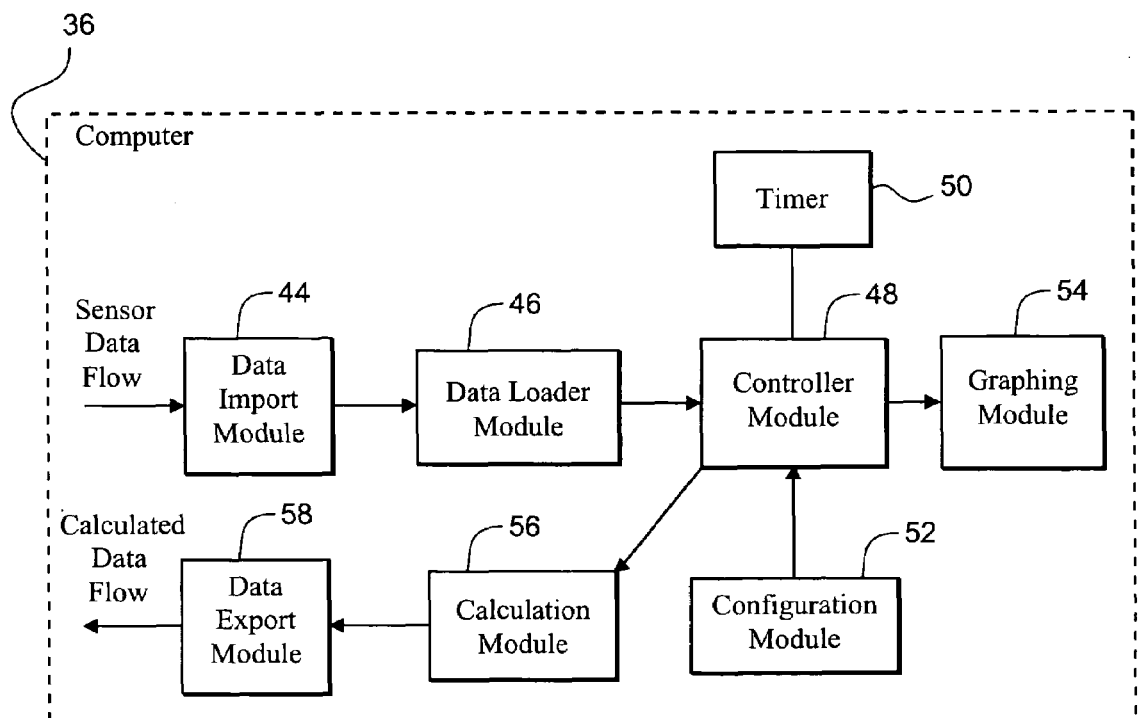
FIG. 3 is a flow chart showing functional software components associated with capturing sensor grid data, processing the data, and generating emission contour maps and other useful data regarding the emissions in the boiler.

FIG. 3 is a flow chart that generally shows the data processing operations performed by the computer 36. The process steps shown in FIG. 3 are performed by the display software 40 and contour graphing software 42, in conjunction with other software modules executed by the computer. Suitable display software, contour graphing software and other software executed by the computer are either conventional and commercially available software programs or may be developed using well-known software programming techniques. The sensor data flow is downloaded into the computer 36 using a software data input module 44. The data import module imports sensor measurement data, e.g., data regarding CO, $O_2$ and/or temperature. Once imported into the computer 36, the sensor data is available for graphing and calculations. Further, the data import module may interrogate the database of sensor readings and time of readings stored in the data acquisition hardware/software 32, 34. The data input module may also include software for downloading sensor data flow over the network connection 38.

The downloaded sensor data is formatted into a database or other form usable by the display software and contour graphing software by a data loader module software program 46. The data loader module temporarily stores the downloaded sensor data and time data so as to provide a database of sensor data usable to generate contour maps of emission levels in the boiler and to calculate emission conditions, such as an average emission level based on an average of sensor readings during a particular period of time.

A controller module 48 in the computer 36 provides control functions for manipulating and calculating the sensor data provided by the data loader module 46. The controller module is provides an interface between the other software modules to allow the modules to function together. The controller module interrogates the other modules and controls the flow data and commands between these modules. In addition, the controller module includes user interface functions which allow the boiler engineer to select a type of graph or map to be used in presenting the data, select a time (or period of times) corresponding to the sensor data to be presented, and select calculations to be performed on the sensor data. For example, a combustion engineer may request contour maps to be prepared based on real time sensor data flow. Further, maps of historical sensor data may be read in from a data file representing data collected at earlier time periods, such as at fifteen minute intervals during a preceeding four hour period. The historical contour maps may be displayed sequentially.

The controller module accesses the data loader module 36 to collect real time sensor data and historical sensor data for each fifteen minute period during a proceeding four hour period. A timer software module 50, may be used to provide a timing function for a real-time sensor data stream and to continually update, e.g., every ten seconds, every second, every $\frac{1}{10}^{th}$ of a second (for example), graphs and plots of the boiler emissions. In addition, the timer 50 may provide timing information to be associated with a real time data flow from the sensor data, if the data acquisition hardware 32 and data acquisition software 34 does not already provide such a timing function. The time module 50 provides timing control for contour plot updates and sets a delay period between each update.

A configuration module 52 works in conjunction with the controller module 58 to format the sensor data and timing information in a manner suitable for either a graphing software module 54 and a data calculation module 56. A certain amount of configuration is needed to, for example, correlate sensor data points from the sensor grid to points on a contour plot or other graph. The configuration module may also establish a graphing update rate, and other parameters needed to be configured. A configuration data file may be stored regarding the sensor points on the grid, refresh rate and other information needed for plotting contour plots. The configuration module 52 may also perform standard data formatting processes to place the sensor data and timing information in a format suitable for graphing the data onto a contour map or presenting the data to a calculation function that generates, for example, average emission levels.

The graphing module 54 generates a map or graph of the sensor data which is viewable by the boiler engineer. By viewing the map or graph of the sensor data, the boiler engineer sees a graphical representation of the actual emission conditions at the plane of the flue gas corresponding to the sensor grid 30. By interacting with the controller module 48, the boiler engineer may alternately view a real time contour map of current sensor data and a sequence of contour maps of prior sensor data readings, such as taking at fifteen minute intervals during the proceeding two hour period.

The boiler engineer may view calculated emission values, such as average emission levels based on an average of all sensor data readings from the grid 30 at current levels and proceeding time intervals, by viewing the output of the calculation module 56. Further, a data export module 57 enables the boiler engineer to export calculated values regarding emissions and based on sensor data from the computer 36 to another computer or, a printer, or other data output devices.

Figure 4:
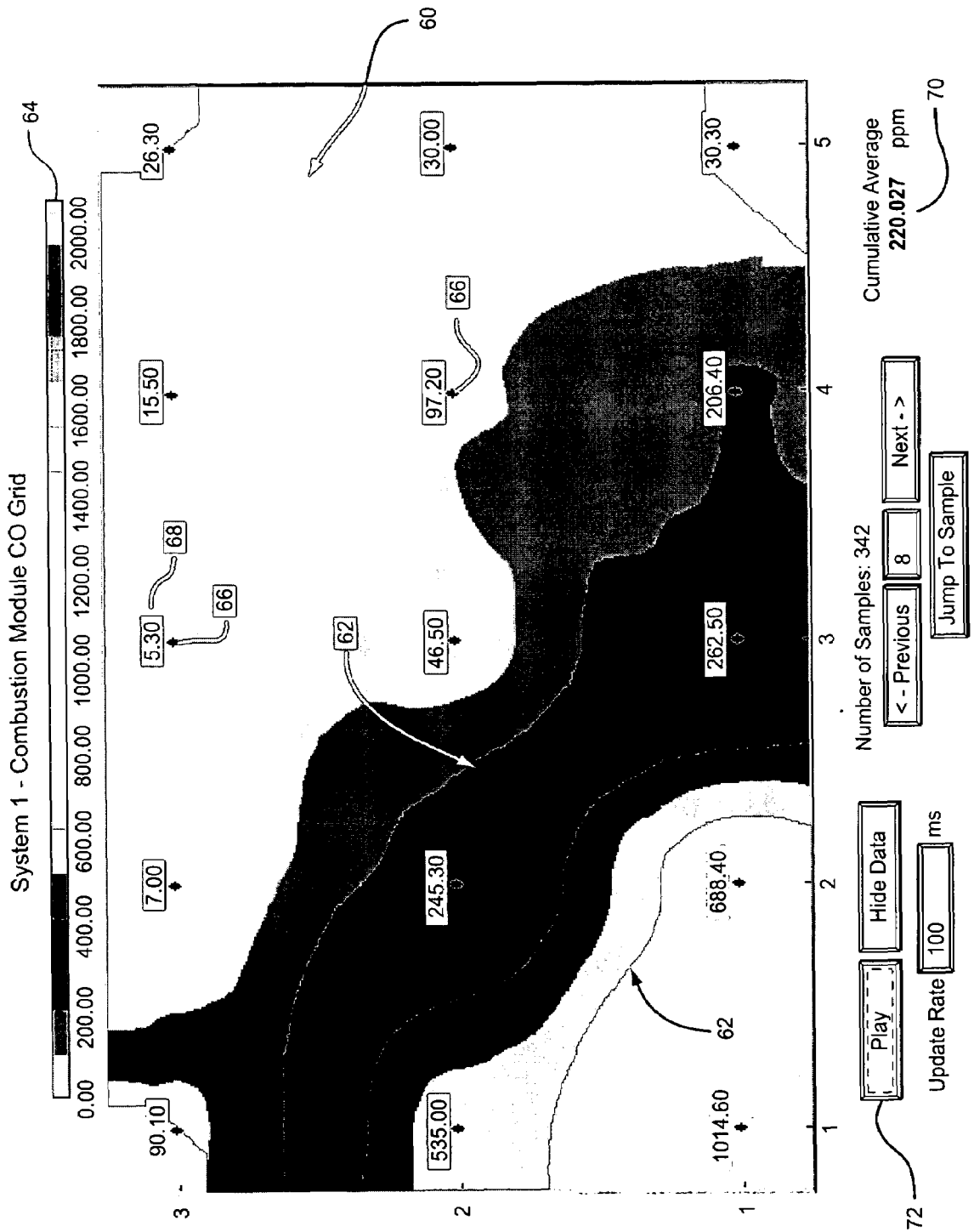
FIGS. 4 and 5 are exemplary contour plots of sensor grid data, wherein the plots are representative of emissions levels at different periods of time.
Figure 5:
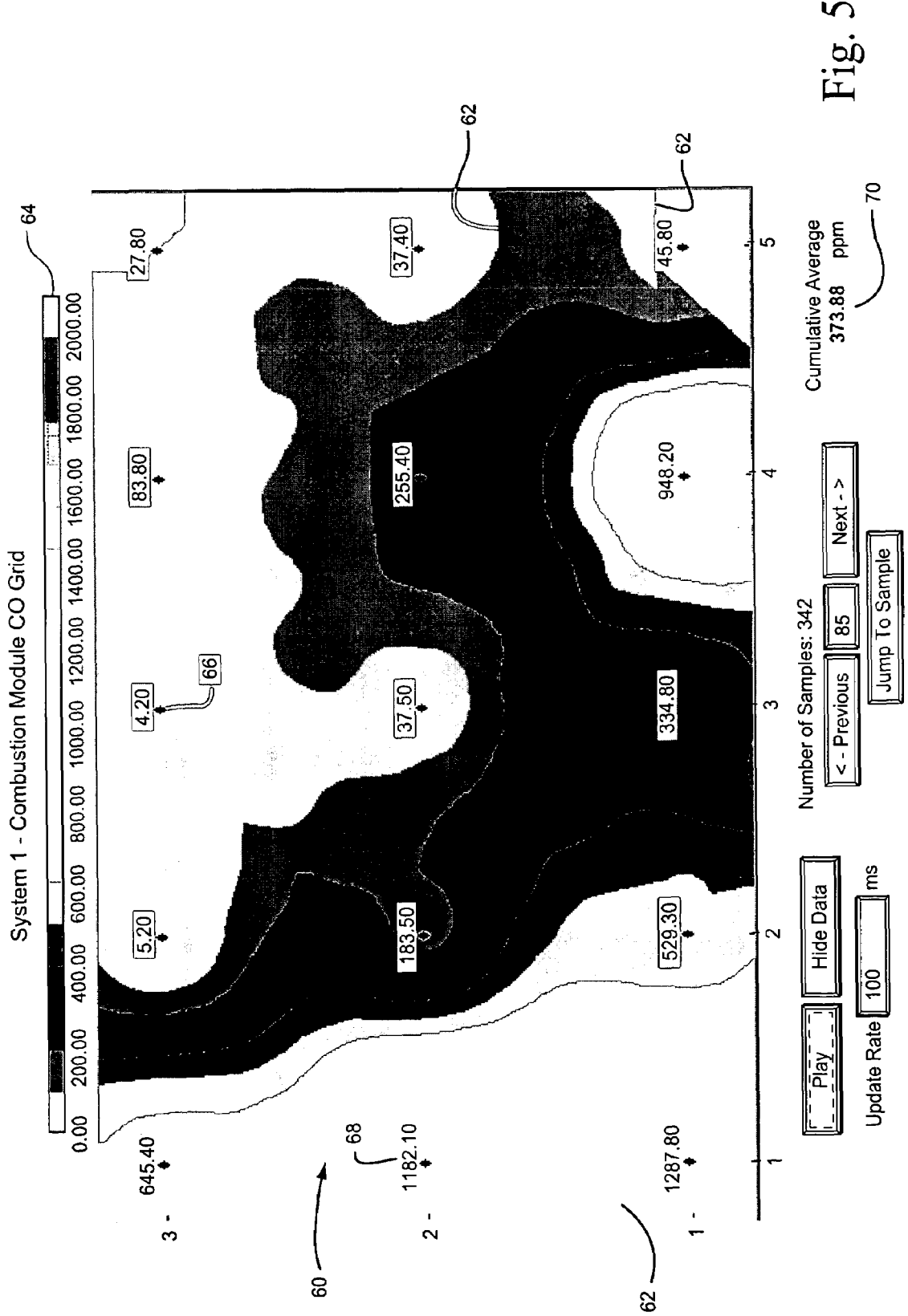

FIGS. 4 and 5 are exemplary contour plot graph of CO emission levels taken by a grid of CO sensors in the flue gas path of a boiler. The plot graphically shows the CO emissions across a flue gas plane of a boiler having a rectangular cross section. The contour plot 60, 62 indicates different levels of CO emissions by shaded or colored regions. A color or gray scale bar 64 at the top of the contour provides a correlation between plot color/shading and emission levels.

The individual sensors in the sensor grid 30 are represented by point 66 on the contour plot. The sensor point 66 are arranged similarly to the arrangement of sensors in the grid 30 in the boiler. The contour plot may also display the actual sensor value 68 for each sensor in the grid. An average sensor reading 70 may be presented below the grid.

The contour graphing module may make available to the boiler engineer a series of contour plots taken at certain intervals, such as every one second, to enable the boiler engineer to see a sequence of changes made to the emission levels as the boiler engineer adjusts combustion conditions in the boiler. In addition, the contour graphing software program may enable a moving picture display 72 which sequentially shows the contour plots over a period of time. The moving picture display readily shows how changes in emission levels occur as adjustments are made to the combustion conditions.

Using the contour plots and cumulative CO average emission level, a boiler engineer is aided in adjusting the combustion conditions to balance the sensor readings 68 in the grid 30 and minimize the cumulative average 70 of the sensor readings. The boiler engineer may use the contour plots and calculated average of the sensor readings to perform other optimization procedures on the boiler. For example, the engineer may adjust boiler controls to reduce smooth the emission gradients shown in a real-time contour plot. By smoothing the gradients on the plot, the tendency can be minimized of the boiler to foul due to reduce pressure zones in the gas duct 14.

Real time CO grid sensor data is presented a graphical form to boiler engineer as they make adjustments to optimize boiler performance. Data from a grid of Reuter-Stokes™ CO sensors 30 is imported into a system through a Reuter-Stokes™ data acquisition unit 34. Once the data is in computer 36, a contour-plotting program will be launched. The plotting application will read the CO data and plot a contour diagram for the sensors in the grid. The plotting software will continuously update this plot with live data. The plot will be arranged with the data points in the same configuration as the CO grid. A single point on the plot will correspond to a single CO sensor in the grid. This graphical representation of the CO sensor data can be used to make adjustments to the boiler to optimize the efficiency of the boiler and to reduce NOx emissions. A service engineer could take a laptop, utilizing CatS Ethernet or wireless networking technology, and stand in front of the boiler controls while viewing the data. The engineer could make adjustments to the boiler and watch the changes in the plots to visually see how his changes affected the boiler performance. The data would be updated in a matter of seconds, providing rapid feedback to the engineer, and thus, minimizing the time to optimize the boiler settings.

The plots will allow the engineers to adjust the combustion fuel nozzles and air injectors (see device 16 in FIG. 1) until the CO sensor values are balanced, and the average CO value is minimized. Achieving balanced sensor values and a minimized averaged sensor value optimizes the combustion conditions for the boiler. To make the adjustments, the engineer may access live sensor data from the data acquisition system, plot the data, calculate an overall CO sensor value, and provide current and historical plots of sensor data in a display package that can be installed on a laptop computer that the boiler engineer carries when making the adjustments at the boiler.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of presenting a changing combustor condition comprising:
   a. sensing the combustor condition using a sensor array in a gas path of the combustor;
   b. generating data from the sensor array representative of the combustor condition at a plurality of positions in the gas path;
   c. transmitting the generated data to a computer system proximate to a control interface for the combustor;
   d. generating a graphical representation of the showing combustion product conditions in the gas path;
   e. displaying the graphical representation on the computer system;
   f. adjusting combustion controls at the control interface to change the combustor conditions, and
   g. repeating steps (a) to (d) to accjuire a sequence of graphical representations of the combustion product conditions over a period of time.

2. A method as in claim 1 wherein the graphical representation is a contour plot.

3. A method as in claim 1 wherein the graphical representation is a contour plot which is updated periodically to provide a real-time representation to the display.

4. A method as in claim 1 wherein the graphical representation is a contour plot which is updated at least every ten seconds.

5. A method as in claim 1 wherein the graphical representation is a contour plot which is updated at least every second.

6. A method as in claim 1 wherein the graphical representation is a contour plot which is updated periodically, and said method further comprises a calculation of an average sensor measurement that is displayed in conjunction with the graphical representation.

7. A method as in claim 1 wherein the data is transmitted periodically in near real-time.

8. A method as in claim 1 wherein the data is transmitted through a network connection.

9. A method as in claim 1 wherein the combustor condition is selected from a group consisting of CO, $O_2$ and temperature.

10. A method of presenting a changing combustor condition comprising:
    a. sensing the combustor condition in near real time using a sensor array in a gas path of the combustor;
    b. generating data from the sensor array representative of the combustor condition at a plurality of positions in the gas path;
    c. transmitting the generated data in near real-time to a computer system, where the computer system is at a location proximate to a control interface for the boiler;
    d. generating a graphical representation of the near real time showing combustor conditions in the gas path;
    e. displaying the graphical representation in near real time on the computer system;
    f. repeating steps (a) to (d) periodically to acquire generated data form the sensor array at a plurality of different times, and
    g. displaying a sequence of graphical representations of combustor conditions at each of the different times.

11. A method as in claim 10 wherein the graphical representation is a contour plot.

12. A method as in claim 10 wherein the graphical representation is a contour plot which is updated periodically.

13. A method as in claim 10 wherein the graphical representation is a contour plot which is updated at least every ten seconds.

14. A method as in claim 10 wherein the graphical representation is a contour plot which is updated at least every second.

15. A method as in claim 10 wherein the graphical representation is a contour plot which is updated periodically, and said method further comprises a calculation of an average sensor measurement that is displayed in conjunction with the graphical representation.

16. A method as in claim 10 wherein the data is transmitted through a network connection.

17. A method as in claim 10 wherein the combustor condition is selected from a group consisting of CO, $O_2$ and temperature.

18. A system for collecting and presenting a changing combustor condition in a boiler comprising:
    a sensor grid located in a combustion product gas path in the boiler, said grid sensing the combustor condition in real time using a sensor array in the gas path and generating data representative of the combustor condition at a plurality of positions in the gas path and at a plurality of different times;
    a network for communicating electronic data;
    a computer system coupled to the network and further comprising a controller and a display, wherein said controller receives the generated data and generates a graphical representations of the real time showing combustor conditions in the gas path and of a sequence of prior combustor conditions in the gas path, and said graphical representation is presented on said display.

19. A system as in claim 18 wherein said computer system is proximate to controls for said combustion system.

20. A system as in claim 18 wherein said graphical representation is a contour plot.

* * * * *